United States Patent
Han et al.

(10) Patent No.: US 9,938,578 B2
(45) Date of Patent: Apr. 10, 2018

(54) MULTIPLEX PYROSEQUENCING USING NON-INTERFERING NOISE CANCELLING POLYNUCLEOTIDE IDENTIFICATION TAGS

(71) Applicants: Jian Han, Huntsville, AL (US); Chunlin Wang, Menlo Park, CA (US)

(72) Inventors: Jian Han, Huntsville, AL (US); Chunlin Wang, Menlo Park, CA (US)

(73) Assignee: iRepertoire, Inc., Huntsville, AL (US)

( * ) Notice: Subject to any disclaimer, the term of this patent is extended or adjusted under 35 U.S.C. 154(b) by 222 days.

(21) Appl. No.: 14/035,686

(22) Filed: Sep. 24, 2013

(65) Prior Publication Data

US 2014/0094376 A1 Apr. 3, 2014

Related U.S. Application Data

(60) Provisional application No. 61/705,089, filed on Sep. 24, 2012.

(51) Int. Cl.
*C12Q 1/68* (2006.01)

(52) U.S. Cl.
CPC ......... *C12Q 1/6881* (2013.01); *C12Q 1/6869* (2013.01)

(58) Field of Classification Search
None
See application file for complete search history.

(56) References Cited

U.S. PATENT DOCUMENTS

2011/0257031 A1  10/2011  Bodeau et al.
2013/0274117 A1* 10/2013  Church ............... C12Q 1/6869
                                                           506/4

FOREIGN PATENT DOCUMENTS

JP    2006163546    6/2006
WO    WO 2012/048341    4/2012

OTHER PUBLICATIONS

International Search Report and Written Opinion issued by the United States Patent and Trademark Office as the International Searching Authority for International Application No. PCT/US2013/061460, entitled Multiplex Pyrosequencing using Non-Interfering Noise-Canceling Polynucleotide Identification Tags; Young, Lee W. (Dec. 17, 2013).
English translation of Abstract for JP 2006163546, entitled Analyzing Device and Compressing Device for Biological Information; Modegi, Toshio (Jun. 22, 2006).

* cited by examiner

*Primary Examiner* — David C Thomas
(74) *Attorney, Agent, or Firm* — Maynard Cooper & Gale, P.C.; Matthew J. Parker

(57) ABSTRACT

The present disclosure generally pertains to a multiplex method for analyzing samples comprising using polynucleotide amplification to produce amplified products wherein one or more target sequences are tagged with a non-interfering, non-canceling target-specific polynucleotide identification tag, pyrosequencing the amplified products through the non-canceling target-specific polynucleotide identification tag sequence to detect the presence of one or more specific polynucleotide identification tags. The presence of a specific polynucleotide identification tag being correlated with the presence of a specific target sequence.

16 Claims, 1 Drawing Sheet

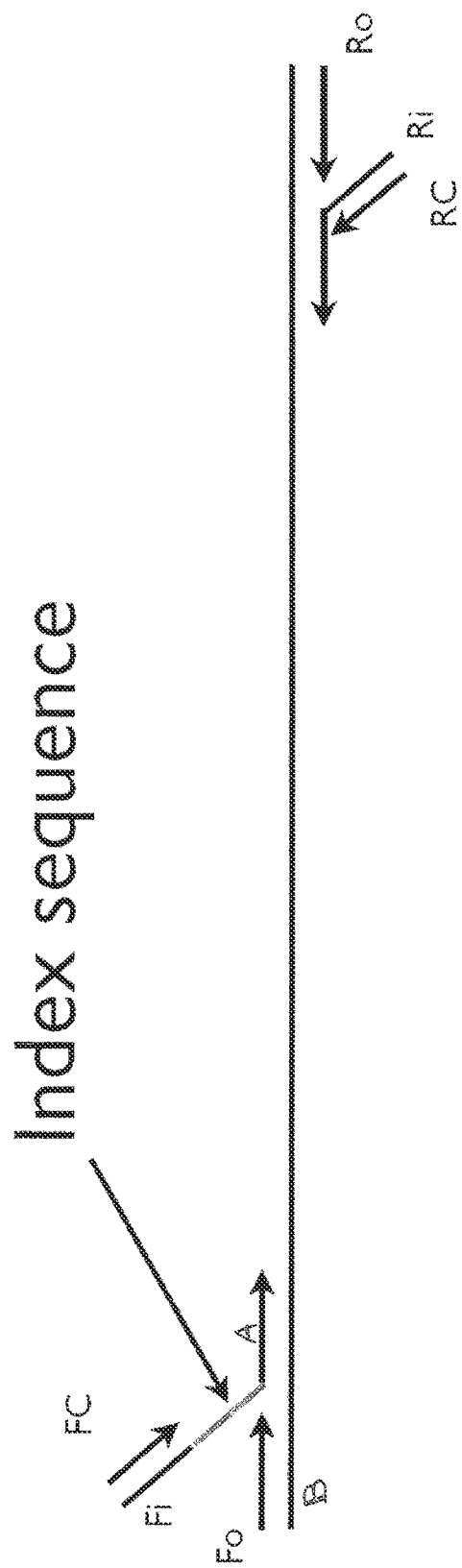

SEQUENCE LISTING

```
<160> NUMBER OF SEQ ID NOS: 60

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 1
aacatggcta                                                          10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 2
aatgcgaatg                                                          10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 3
aatgtccatg                                                          10
```

```
<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 4
aattgcaatg                                                           10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 5
acttgcatgg                                                           10

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 6
atccatggtg                                                           10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 7
atggcttggc                                                           10

<210> SEQ ID NO 8
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 8
cagccttcca                                                           10

<210> SEQ ID NO 9
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 9
ccaatatgtc                                                           10
```

```
<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 10
ccatgccttg                                                           10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 11
cctcaagatc                                                           10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 12
ccttcaagca                                                           10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 13
ctcttggcca                                                           10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 14
gaattctggc                                                           10

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 15
gatggtggaa                                                           10
```

```
<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 16
gcaagaattg                                                                10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 17
gcaggaattc                                                                10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 18
gccaagaatc                                                                10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 19
gccattggcc                                                                10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 20
gcggccatgg                                                                10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 21
ggaatggcaa                                                                10

<210> SEQ ID NO 22
```

```
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 22
ggccgaatgc                                                              10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 23
ggtggcatta                                                              10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 24
taatggtgca                                                              10

<210> SEQ ID NO 25
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 25
tcattgctgg                                                              10

<210> SEQ ID NO 26
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 26
tgcttcaatg                                                              10

<210> SEQ ID NO 27
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 27
tgttgcattc                                                              10

<210> SEQ ID NO 28
<211> LENGTH: 10
```

```
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 28
ttcattatgc                                                              10

<210> SEQ ID NO 29
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 29
ttctgccatg                                                              10

<210> SEQ ID NO 30
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 30
ttggcagcgc                                                              10

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 31
aagccatgcc                                                              10

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 32
aatggtgcaa                                                              10

<210> SEQ ID NO 33
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 33
aattcatatg                                                              10

<210> SEQ ID NO 34
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      NINC polynucleotide identification tag

<400> SEQUENCE: 34
aattgcggca                                                          10

<210> SEQ ID NO 35
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 35
atatgtccaa                                                          10

<210> SEQ ID NO 36
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 36
atggatcttc                                                          10

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 37
caagccttgc                                                          10

<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 38
ccaagatcaa                                                          10

<210> SEQ ID NO 39
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 39
ccaattcaca                                                          10

<210> SEQ ID NO 40
<211> LENGTH: 10
<212> TYPE: DNA
<213> ORGANISM: Artificial Sequence
```

```
<220> FEATURE:
<223> OTHER INFORMATION: Description of Artificial Sequence: Synthetic
      NINC polynucleotide identification tag

<400> SEQUENCE: 40
ccattccgca                                                              10

<210> SEQ ID NO 41
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 41
cctgcctgcc                                                              10

<210> SEQ ID NO 42
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 42
ccttggctga                                                              10

<210> SEQ ID NO 43
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 43
ctggattgcc                                                              10

<210> SEQ ID NO 44
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 44
gaggattggc                                                              10

<210> SEQ ID NO 45
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 45
gattccatgg                                                              10

<210> SEQ ID NO 46
<211> LENGTH: 10
<212> TYPE: DNA
<213> ORGANISM: Artificial Sequence
<220> FEATURE:
```

```
<223> OTHER INFORMATION: Description of Artificial Sequence: Synthetic
      NINC polynucleotide identification tag

<400> SEQUENCE: 46
gcaattcttg                                                            10

<210> SEQ ID NO 47
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 47
gccaagaaca                                                            10

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 48
gccaaggcaa                                                            10

<210> SEQ ID NO 49
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 49
gccgccaatg                                                            10

<210> SEQ ID NO 50
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 50
gctgccggcc                                                            10

<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 51
ggacatggaa                                                            10

<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence: Synthetic
```

NINC polynucleotide identification tag

<400> SEQUENCE: 52
ggtcatggcc 10

<210> SEQ ID NO 53
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 53
taatgctgcc 10

<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 54
tcaagcacca 10

<210> SEQ ID NO 55
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 55
tgcattcaac 10

<210> SEQ ID NO 56
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 56
tggatcaatg 10

<210> SEQ ID NO 57
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 57
ttcatcatcc 10

<210> SEQ ID NO 58
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

```
<400> SEQUENCE: 58
ttcattgcaa                                                                10

<210> SEQ ID NO 59
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 59
ttgcagccaa                                                                10

<210> SEQ ID NO 60
<211> LENGTH: 10
<212> TYPE: DNA
<213> ORGANISM: Artificial Sequence
<220> FEATURE:
<223> OTHER INFORMATION: Description of Artificial Sequence: Synthetic
      NINC polynucleotide identification tag

<400> SEQUENCE: 60
ttggcatgga                                                                10
```

MULTIPLEX PYROSEQUENCING USING NON-INTERFERING NOISE CANCELLING POLYNUCLEOTIDE IDENTIFICATION TAGS

CROSS REFERENCE TO RELATED APPLICATION

This application claims priority to U.S. Provisional Patent Application No. 61/705,089, entitled "Multiplex Pyrosequencing Using Non-Interfering Noise-Canceling Polynucleotide Identification Tags," and filed on Sep. 24, 2012, which is incorporated herein by reference.

SEQUENCE LISTING

The instant application contains a Sequence Listing which has been submitted in ASCII format via EFS-Web and is hereby incorporated by reference in its entirety. Said ASCII copy, created on Sep. 23, 2013, is named 15892-0002_SL.txt and is 15,785 bytes in size.

FIELD OF THE INVENTION

The invention relates to methodologies for analyzing and sequencing nucleic acid samples. More specifically, the invention relates to methods for sequencing amplified nucleic acid samples through the use of specific polynucleotide identification tags.

BACKGROUND OF THE INVENTION

The development of nucleic acid amplification methodologies, for instance the polymerase chain reaction (PCR), enables the use of DNA amplification for a variety of uses, including molecular diagnostic testing. There are challenges associated with the use of PCR for molecular differential diagnostic (MDD) assays, however. PCR utilizes specific primers or primer sets, temperature conditions, and enzymes. For example, PCR reactions are easily contaminated, primer binding may require different conditions for different primers and primers should be specific for a target sequence in order to amplify only that target sequence. These limitations make it even more difficult to amplify multiple sequences from a single sample.

Diagnostic testing of clinical samples to find one or more causative disease agents has, in the past, required that microorganisms be isolated and cultured. This may take days, however, and in many cases a diagnosis must be acted upon within hours if the patient's life is to be saved. Analysis of a single clinical sample to identify multiple organisms in order to determine which one(s) may be the causative agent(s) of disease is the desired method for MDD, and methods have been developed to better achieve that goal. For example, multiplex PCR methods have been developed to amplify multiple nucleic acids within a sample in order to produce enough DNA/RNA to enable detection and identification of multiple organisms. Multiplex PCR has disadvantages, however. For example, each target in a multiplex PCR reaction requires its own optimal reaction conditions, so increasing the number of targets requires that the reaction conditions for each individual target are less than optimal. Furthermore, multiple sets of high-concentration primers in a system often generate primer dimmers or give non-specific, background amplification. This lack of specificity also requires the additional steps of post-PCR clean-up and multiple post-hybridization washes.

Crowded primers reduce amplification efficiency by requiring the available enzymes and consuming substrates. Differences in amplification efficiency may lead to significant discrepancies in amplicon yields. For example, some loci may amplify very efficiently, while others amplify very inefficiently or fail to amplify at all. This potential for uneven amplification also makes it difficult to impossible to accurately perform end-point quantitative analysis.

Often, time is of the essence, patient infections include more than one bacterial species, and the amount of the target DNA in a clinical sample is limiting. Technologies such as multiplex PCR have been developed to address these issues. However, improvements in this field are still needed in order to further decrease the time and effort required to accomplish quick and accurate analysis of clinical samples. Methods that can be automated, especially by use of a closed cassette for sample preparation and analysis, are particularly important, as they may provide the added advantages of decreasing potential contamination of samples and decreasing the time and effort that a laboratory technician must invest in preparing and analyzing each sample.

Although there have been significant improvements in multiplex sequencing technologies and their use in sample analysis, it would be highly beneficial if these could be further refined to make analysis and detection easier.

SUMMARY OF THE INVENTION

The present invention relates to a multiplex method for analyzing samples which may comprise mixed DNA or RNA populations, the method comprising using polynucleotide amplification to produce amplified products wherein one or more target sequences are tagged with a non-interfering, non-canceling target-specific polynucleotide identification tag, and pyrosequencing the amplified products through the non-interfering, non-canceling target-specific polynucleotide identification tag sequence to detect the presence of one or more specific polynucleotide identification tags, the presence of a specific polynucleotide identification tag being correlated with the presence of a specific target sequence. In one embodiment, the polynucleotide may comprise DNA, RNA or a mixed DNA/RNA population. In an additional embodiment, the multiplex reaction comprises a PCR reaction.

Aspects of the invention also relate to a multiplex method for analyzing a sample containing one or more unidentified polynucleotides, the method comprising the steps of attaching to a target-specific primer a target-unique non-interfering, non-canceling polynucleotide identification tag, hybridizing the target-specific primer to a target polynucleotide sequence, performing polynucleotide amplification to amplify the target polynucleotide sequence and add the target-unique non-interfering, non-canceling polynucleotide identification tag to the target polynucleotide sequence, and pyrosequencing the target-unique non-interfering, non-canceling target-specific polynucleotide identification tag, wherein identification of a target-unique non-interfering, non-canceling target-specific polynucleotide identification tag indicates the presence of the target polynucleotide. In one embodiment, the polynucleotide may comprise DNA, RNA or a mixed DNA/RNA population. In an additional, the multiplex reaction comprises a PCR reaction.

Aspects of the invention also relate to a multiplex PCR pyrosequencing method wherein the target-unique non-interfering, non-canceling polynucleotide identification tag is chosen from among the group of sequences consisting of SEQ ID NO: 1, SEQ ID NO: 2, SEQ ID NO: 3, SEQ ID NO:

4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, and SEQ ID NO: 60.

One aspect of the invention utilizes nested target-specific primers. Target nucleic acids may comprise DNA and/or RNA, and may comprise DNA and/or RNA of viral, bacterial, and/or fungal origin, as well as genomic DNA and/or RNA of human or other animal origin. Amplification may be performed by polymerase chain reaction (PCR) and/or RT-PCR. The source of the target nucleic acids may be from one or more clinical, environmental, or food samples and the method may be used in a wide variety of ways, including, for example, clinical diagnosis, environmental sampling, plant testing, food safety analysis, detection of genetic disorders, and/or detection of disease conditions. The method may be used for human and/or veterinary medical diagnoses.

BRIEF DESCRIPTION OF THE DRAWINGS

FIG. 1 is an illustration of an example of the method for attaching a target-specific, or target-unique, polynucleotide identification tag using PCR. In FIG. 1, "index tag" denotes the target-specific (target-unique) polynucleotide identification tag. Fo, Fi, Fc, Ro, Ri, and Rc indicate primer sequences and positions.

DETAILED DESCRIPTION

Pyrosequencing is a nucleic acid sequencing technique that is based upon the detection of released pyrophosphate during nucleic acid synthesis. Visible light is generated during this enzymatic reaction that is proportional to the number if incorporated nucleotides. Inorganic pyrophosphate is released as a result of nucleotide incorporation by the enzyme polymerase. In some embodiments, luciferase is utilized to generate light which is easily detected by a photodiode, photomultiplier tube, or a charge coupled device (CCD) camera. The sequence of the template nucleic acid may be determined because the added nucleotide is known. Pyrosequencing is possible with both DNA and RNA. Essentially, the method allows sequencing of a single strand of nucleic acid by synthesizing its complementary strand, one base pair at a time, and detecting which base was added at each step by measuring the light emitted during nucleotide incorporation. Pyrosequencing represents a rapid, accurate method for nucleic acid application from bacterial, viral, fungal, and other similar sources to aid in identifications from clinical samples. However, pyrosequencing is a parallel-sequencing method—generally requiring multiple parallel sequencing runs to analyze a mixed sample. Performing this sequencing method in a single containment vessel, as with the multiplex PCR sequencing method, could significantly reduce the cost and the time required to produce needed results. The inventors have developed a method that will allow pyrosequencing to be performed in a true multiplex manner—sequencing and detecting multiple samples in a single multiplex reaction, rather than multiple parallel reactions.

The inventors realized that the advantage of pyrosequencing—the fact that detection of sequencing results is based on detection of light emitted as released pyrophosphate is generated as nucleotides are added during DNA synthesis—generally rules out the use of multiplex PCR and sequencing because detection of multiple different sequences becomes relatively impossible. However, they have developed a method that overcomes this obstacle. In doing so, they have produced a method for multiplex polynucleotide amplification and pyrosequencing that may be performed within the confines of a single cassette, such as that used in the method described in WO/2010/132834 (Apparatus for Performing Amplicon Rescue Multiplex PCR), which is herein incorporated by reference in its entirety.

It is to be understood that the term "comprising," as used herein, may be substituted with the terms "consisting essentially of" and "consisting of." Where the term "reaction system" is used, it is intended to describe an Eppendorf tube, reaction chamber, or other containment device into which the necessary primers, enzymes, nucleotides, buffers, and/or other reagents are placed in order to perform one or more cycles of at least one polymerase chain reaction. A different "reaction system" may therefore refer to the same reaction containment vessel, but a different component of reagents—particularly primers—for performing the desired amplification step. A "reaction containment vessel" is intended to mean a tube, plate well, or other vessel having a sufficient internal volume to contain primers, enzymes, nucleotides, buffers, and/or other reagents necessary to provide a reaction system. The term "rescue" is intended to mean the separation of amplicons from at least a portion of the primers of the first amplification. "PCR" is intended to mean the polymerase chain reaction, and may include PCR and/or RT-PCR procedures.

In one embodiment, the presently described method includes using polynucleotide amplification to produce amplified products wherein one or more target sequences are tagged with a non-interfering, non-canceling target-specific polynucleotide identification tag. A "non-interfering, non-canceling target-specific polynucleotide identification tag", as defined herein, refers to a polynucleotide sequence which, when bound to a target sequence or a primer, will not interfere with the function of a polymerase enzyme, alter the nucleotide structure located at the end of the nucleotide template or primer, interfere with primer annealing to the template, introduce complex structures in the target polynucleotide, or otherwise interfere with or prevent the binding of primers and/or amplification of the target nucleotide. The presently described methods may utilize DNA samples, RNA targets, or targets with a mixed DNA/RNA population. In additional embodiments, the disclosed methods may employ PCR and/or reverse transcription polymerase chain reaction (RT-PCR) for the amplification of polynucleotides.

In one embodiment, amplification of products including target sequences tagged with an identification tag may be accomplished utilizing amplicon rescue multiplex polymerase chain reaction, as described in WO/2009/124293, and utilizing them methods and apparatus described in WO/2010/132834, the contents of each are incorporated herein by reference in their entireties. Briefly, high-concentration, target-specific, nested primers are used to perform a target-specific first amplification procedure. Target-specific primers may be used to amplify one or more (and preferably multiple) target nucleic acids of bacterial, viral, fungal, and/or other origin, for example. The target nucleic acids may be of human or animal origin. In one embodiment, the target nucleic acids originate from a human clinical sample. As illustrated in FIG. 1, a forward primer $F_i$ is attached to or "tagged" with additional nucleotides to provide an additional sequence that is not specific for the target nucleic acid(s) so that amplification of the target nucleic acid B with such a primer will also incorporate into the resulting amplicon a non-interfering, non-canceling target-specific polynucleotide identification tag, referred to in FIG. 1 as the "Index Sequence". In one embodiment, the non-interfering, non-canceling target-specific polynucleotide identification tag is selected from those listed in Table 1. The method incorporates additional primers FC and $F_o$, the functions of which are described in detail in WO/2009/124293. Amplification is performed, the reaction is terminated, and the resulting amplicons are rescued from the reaction mix described in detail in WO/2009/124293 for use in a pyrosequencing procedure. The pyrosequencing is performed in a different reaction system, which may or may not utilize the same reaction containment vessel.

In the embodiment illustrated in FIG. 1, these tags are individually paired with a specific target sequence by synthesizing a polynucleotide comprising a primer sequence $F_i$, a polynucleotide identification tag or index sequence, and a target-specific sequence A that will hybridize with the desired target polynucleotide sequence B. The tag is chosen to correlate with a particular target sequence. Specifically, the amplification reactants include a forward primer sequence $F_i$ which is attached to or "tagged" with additional nucleotides, i.e., the polynucleotide identification tag or index sequence which is not specific for the target nucleic acid(s), and a target specific sequence A. The target specific primer $F_i$/identification tag is then hybridized to the target polynucleotide sequence B and amplification is initiated by a known method, for instance PCR and/or RT-PCR. The resulting amplification of the target nucleic acid B with such a primer will incorporate into the resulting amplicon the non-interfering, non-canceling target-specific polynucleotide identification tag. Using the synthesized polynucleotide, the primer sequence and polynucleotide identification tag sequence may be incorporated into the 5'-end of a polynucleotide produced as an amplification product.

The method further includes pyrosequencing the amplified products through the non-canceling target-specific polynucleotide identification tag sequence to detect the presence of one or more specific polynucleotide identification tags. Here, the presence of a specific polynucleotide identification tag is correlated with the presence of a specific target sequence. To accomplish this, the inventors have developed a series of 10 base pair sequences that may be sequenced within the same reaction chamber using pyrosequencing—without creating confusing signals as the identification tags are sequenced (see Table 1). That amplification product may then be pyrosequenced through the polynucleotide identification tag sequence. The presence of the corresponding polynucleotide identification tag sequence therefore correlates with the presence of a specific target sequence, and the identification of the target in a sample, such as a clinical sample, can be performed without completing the sequencing reaction for the entire target polynucleotide.

As the polynucleotide identification tags are sequenced in the multiplex pyrosequencing reaction, light generated through the enzymatic release of inorganic pyrophosphate as a result of nucleotide incorporation with polymerase may be detected using a photodiode, photomultiplier tube, or charge-coupled device camera, for example. The nature of the non-interfering, non-canceling target-specific polynucleotide identification tag sequences is such that they will not interfere with distinct individual detection of the tags as they are sequenced in the same reaction container.

The result is a faster method for identifying unknowns in a clinical sample, for example. By pairing this method with a method such as the armPCR method described in WO/2009/124293, for example, and using a device such as that described in WO/2010/132834, it is now possible to achieve an automated, single-cassette, polynucleotide amplification and sequencing procedure that can be performed, along with detection, within a single machine into which one or more cassettes may be inserted. Results may be returned in significantly less time because it is only necessary to sequence a few base pairs, rather than tens or hundreds of base pairs.

Polynucleotide identification tags which the inventors have determined to be non-interfering and non-canceling are shown in Table 1.

TABLE 1

| |
|---|
| AACATGGCTA (SEQ ID NO: 1) |
| AATGCGAATG (SEQ ID NO: 2) |
| AATGTCCATG (SEQ ID NO: 3) |
| AATTGCAATG (SEQ ID NO: 4) |
| ACTTGCATGG (SEQ ID NO: 5) |
| ATCCATGGTG (SEQ ID NO: 6) |
| ATGGCTTGGC (SEQ ID NO: 7) |
| CAGCCTTCCA (SEQ ID NO: 8) |
| CCAATATGTC (SEQ ID NO: 9) |
| CCATGCCTTG (SEQ ID NO: 10) |
| CCTCAAGATC (SEQ ID NO: 11) |
| CCTTCAAGCA (SEQ ID NO: 12) |
| CTCTTGGCCA (SEQ ID NO: 13) |
| GAATTCTGGC (SEQ ID NO: 14) |
| GATGGTGGAA (SEQ ID NO: 15) |
| GCAAGAATTG (SEQ ID NO: 16) |
| GCAGGAATTC (SEQ ID NO: 17) |
| GCCAAGAATC (SEQ ID NO: 18) |
| GCCATTGGCC (SEQ ID NO: 19) |
| GCGGCCATGG (SEQ ID NO: 20) |
| GGAATGGCAA (SEQ ID NO: 21) |
| GGCCGAATGC (SEQ ID NO: 22) |
| GGTGGCATTA (SEQ ID NO: 23) |
| TAATGGTGCA (SEQ ID NO: 24) |
| TCATTGCTGG (SEQ ID NO: 25) |
| TGCTTCAATG (SEQ ID NO: 26) |

TABLE 1-continued

| | |
|---|---|
| TGTTGCATTC (SEQ ID NO: 27) | GAGGATTGGC (SEQ ID NO: 44) |
| TTCATTATGC (SEQ ID NO: 28) | GATTCCATGG (SEQ ID NO: 45) |
| TTCTGCCATG (SEQ ID NO: 29) | GCAATTCTTG (SEQ ID NO: 46) |
| TTGGCAGCGC (SEQ ID NO: 30) | GCCAAGAACA (SEQ ID NO: 47) |
| AAGCCATGCC (SEQ ID NO: 31) | GCCAAGGCAA (SEQ ID NO: 48) |
| AATGGTGCAA (SEQ ID NO: 32) | GCCGCCAATG (SEQ ID NO: 49) |
| AATTCATATG (SEQ ID NO: 33) | GCTGCCGGCC (SEQ ID NO: 50) |
| AATTGCGGCA (SEQ ID NO: 34) | GGACATGGAA (SEQ ID NO: 51) |
| ATATGTCCAA (SEQ ID NO: 35) | GGTCATGGCC (SEQ ID NO: 52) |
| ATGGATCTTC (SEQ ID NO: 36) | TAATGCTGCC (SEQ ID NO: 53) |
| CAAGCCTTGC (SEQ ID NO: 37) | TCAAGCACCA (SEQ ID NO: 54) |
| CCAAGATCAA (SEQ ID NO: 38) | TGCATTCAAC (SEQ ID NO: 55) |
| CCAATTCACA (SEQ ID NO: 39) | TGGATCAATG (SEQ ID NO: 56) |
| CCATTCCGCA (SEQ ID NO: 40) | TTCATCATCC (SEQ ID NO: 57) |
| CCTGCCTGCC (SEQ ID NO: 41) | TTCATTGCAA (SEQ ID NO: 58) |
| CCTTGGCTGA (SEQ ID NO: 42) | TTGCAGCCAA (SEQ ID NO: 59) |
| CTGGATTGCC (SEQ ID NO: 43) | TTGGCATGGA (SEQ ID NO: 60) |

What is claimed is:

1. A multiplex amplification method for analyzing samples which may comprise mixed polynucleotide populations, the method comprising:
    amplifying one or more target polynucleotide sequences using target-specific primers tagged with non-interfering, non-canceling target-unique polynucleotide identification tags wherein the one or more amplified target polynucleotide sequences each incorporate a non-interfering, non-canceling target-unique polynucleotide identification tag; and
    pyrosequencing the one or more non-interfering, non-canceling target-unique polynucleotide identification tags, wherein the presence of a specific polynucleotide identification tag is correlated with the presence of a specific target polynucleotide sequence;
    wherein the amplification and pyrosequencing take place within the same reaction containment vessel.

2. The method of claim 1, wherein the polynucleotide population comprise RNA.

3. The method of claim 1, wherein the polynucleotide amplification comprises PCR.

4. The method of claim 1, wherein the polynucleotide amplification comprises RT-PCR.

5. The method of claim 1, wherein the non-interfering, non-canceling target-unique polynucleotide identification tag is chosen from among the group of sequences consisting of SEQ ID NO: 1, SEQ ID NO: 2, SEQ ID NO: 3, SEQ ID NO:4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, and SEQ ID NO: 60.

6. The method of claim 1, wherein the one or more target sequences are bacterial nucleic acids.

7. The method of claim 1, wherein the one or more target sequences are obtained from a human clinical sample.

8. The method of claim 1, wherein the one or more target sequences are obtained from a clinical sample from an animal.

9. A method comprising the steps of:
    attaching to a target-specific primer a non-interfering, non-canceling target-unique polynucleotide identification tag;
    hybridizing the target-specific primer to a target polynucleotide sequence;
    performing polynucleotide amplification to amplify the target polynucleotide sequence and incorporate the target-unique polynucleotide identification tag into the amplified target polynucleotide sequence; and
    pyrosequencing the target-unique non-interfering, non-canceling polynucleotide identification tag, wherein identification of a target-unique non-interfering, non-canceling polynucleotide identification tag indicates the presence of the target polynucleotide;
    wherein the hybridization, amplification and pyrosequencing all take place within the same reaction containment vessel.

10. The method of claim 9, wherein the polynucleotide population comprise RNA.

11. The method of claim 9, wherein the polynucleotide amplification comprises PCR.

12. The method of claim 9, wherein the polynucleotide amplification comprises RT-PCR.

13. The method of claim 9, wherein the non-interfering, non-canceling target-unique polynucleotide identification tag is chosen from among the group of sequences consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, and SEQ ID NO: 60.

14. The method of claim 9, wherein the one or more target sequences are bacterial nucleic acids.

15. The method of claim 9, wherein the one or more target sequences are obtained from a human clinical sample.

16. The method of claim 9, wherein the one or more target sequences are obtained from a clinical sample from an animal.

\* \* \* \* \*